(12) United States Patent
Lan et al.

(10) Patent No.: US 7,661,309 B2
(45) Date of Patent: Feb. 16, 2010

(54) ANGLE AND FORCE MEASUREMENT INSTRUMENT

(75) Inventors: Le-Ngoc Lan, Christchurch (NZ); Andrew Brent Lintott, Christchurch (NZ); Marcus James King, Christchurch (NZ); Julian Kyle Verkaaik, Christchurch (NZ)

(73) Assignee: Industrial Research Limited, Auckland (NZ)

( * ) Notice: Subject to any disclaimer, the term of this patent is extended or adjusted under 35 U.S.C. 154(b) by 0 days.

(21) Appl. No.: 11/576,397

(22) PCT Filed: Oct. 4, 2005

(86) PCT No.: PCT/NZ2005/000257

§ 371 (c)(1),
(2), (4) Date: Dec. 13, 2007

(87) PCT Pub. No.: WO2006/038822

PCT Pub. Date: Apr. 13, 2006

(65) Prior Publication Data

US 2008/0202233 A1    Aug. 28, 2008

(30) Foreign Application Priority Data

Oct. 4, 2004  (NZ) .................... 535737
Jun. 14, 2005  (NZ) .................... 540796

(51) Int. Cl.
*G01L 5/00* (2006.01)
(52) U.S. Cl. ................... 73/379.02
(58) Field of Classification Search ........... 73/379.02, 73/379.01, 379.03, 865.4, 153; 33/366.11; 345/174; 340/573.1; 128/782
See application file for complete search history.

(56) References Cited

U.S. PATENT DOCUMENTS

| 4,665,928 | A | * | 5/1987 | Linial et al. ............. 600/595 |
| 4,909,262 | A |  | 3/1990 | Halpern et al. |
| 4,913,163 | A |  | 4/1990 | Roger et al. |
| 5,050,618 | A |  | 9/1991 | Larsen |
| 5,339,533 | A |  | 8/1994 | Richardson |
| 5,469,862 | A |  | 11/1995 | Kovacevic |
| 5,474,083 | A |  | 12/1995 | Church et al. |

(Continued)

FOREIGN PATENT DOCUMENTS

EP      0 336 030 A      10/1989

(Continued)

*Primary Examiner*—Jewel Thompson
(74) *Attorney, Agent, or Firm*—Frommer Lawrence & Haug LLP; Ronald R. Santucci

(57) ABSTRACT

A portable handheld device (20) for use by a therapist to measure angles and forces associated with a joint of a patient. The device (20) comprises a housing (22) with a contact pad (26) that is arranged to contact a body part associated with the joint and a hand piece (24) for the therapist to grip. A goniometer is mounted within the housing (22) and is arranged to measure the angular position of the body part when it is in contact with the contact pad (26) and generate representative angle data. A force sensor is coupled to the contact pad (26) and is arranged to measure the force applied by the body part to the contact pad (26) and generate representative force data. A control system is also provided and is arranged to operate the goniometer and force sensor simultaneously to capture measurements of angle data and force data simultaneously.

39 Claims, 13 Drawing Sheets

U.S. PATENT DOCUMENTS

| | | | |
|---|---|---|---|
| 5,935,086 A | 8/1999 | Beacon et al. | |
| 6,059,506 A * | 5/2000 | Kramer | 414/5 |
| 6,148,280 A * | 11/2000 | Kramer | 702/153 |
| 6,413,229 B1 | 7/2002 | Kramer et al. | |
| 6,551,258 B1 | 4/2003 | Herling et al. | |
| 6,792,801 B2 * | 9/2004 | Hoggan et al. | 73/379.02 |
| 6,871,413 B1 * | 3/2005 | Arms et al. | 33/366.11 |
| 6,995,752 B2 * | 2/2006 | Lu | 345/174 |
| 7,365,647 B2 * | 4/2008 | Nativ | 340/573.1 |
| 2004/0107592 A1 | 6/2004 | Matlis | |
| 2004/0134274 A1 | 7/2004 | Hoggan et al. | |

FOREIGN PATENT DOCUMENTS

| | | |
|---|---|---|
| EP | 0 710 466 A | 5/1996 |
| WO | WO 86/05404 | 9/1986 |
| WO | WO 94/26359 | 11/1994 |

* cited by examiner

ANGLE AND FORCE MEASUREMENT INSTRUMENT

BACKGROUND TO THE INVENTION

Physiotherapists often need to assess a person's strength and range of motion in order to gauge the extent of a person's ability, rate of recovery, and the effectiveness of a particular physiotherapy regime.

Currently the assessment is based on functionality, e.g. the MRC scale for grading muscle strength, and is somewhat subjective. For example, one criterion is whether the subject can raise their forearm against the force of gravity. The subject will either be able to achieve this or not, although some credit is given for almost achieving it. A combination of simple tests of this kind combined with a subjective strength assessment obtained from physically resisting the subject's limbs through a range of motion leads to a score or index from 0 to 5 that describes the strength and functionality of the patient.

The advantage of this type of assessment is that it sums up a patient's ability in a single number. This can also be a disadvantage as it encompasses a number of criteria, hiding the subtleties of the subject's profile of abilities, and cannot be used as an accurate gauge of progress.

It is also known to use isokinetic dynamometers to measure muscle strength across the range of motion that a patient has. This is achieved by a torque sensor arm being driven in an arc by a variable speed motor. The patient pushes against the arm through the range of motion. A pair of graphs is produced that records torque and angle of the arm.

Other devices have also been developed to assist in the assessment of a person's strength and range of motion. For example, U.S. Pat. No. 6,792,801 describes a handheld apparatus that is capable of testing isometric muscle strength in one mode and range of motion in another mode.

It is an object of the present invention to provide an improved instrument for measuring the angles and forces associated with a joint of a person, or to at least provide the public with a useful choice.

SUMMARY OF THE INVENTION

In a first aspect, the present invention broadly consists in a portable handheld device for measuring angles and forces associated with a joint of a person, comprising: a housing with a contact surface that is arranged to contact a body part associated with the joint; a goniometer associated with the housing that is arranged to measure the angular position of the body part when it is in contact with the contact surface of the housing and generate representative angle data; a force sensor associated with the housing that is arranged to measure the force applied by the body part to the contact surface of the housing and generate representative force data; and a control system associated with the housing that is arranged to operate the goniometer and force sensor simultaneously to capture measurements of angle data and force data simultaneously.

Preferably, the control system may comprise external interfaces and may be operable to transfer the angle data and force data to external devices via the external interfaces.

Preferably, the control system may comprise memory and may be arranged to store the angle data and force data in the memory.

Preferably, the control system may comprise a user interface that may be operable by a user to control the device and manipulate the angle data and force data.

Preferably, the control system may comprise an output display that may be incorporated into the housing to display the angle data and force data. For example, the control system may be operable to display the angle data and force data graphically against each other on the output display to provide an indication of the strength of the joint over a range of motion. Additionally or alternatively, the control system may be operable to display the angle data and force data graphically against time on the output display. Additionally or alternatively, the control system may be operable to process the angle data and force data to generate and display one or more discrete measurements on the output display, the discrete measurements comprising any one or more of the following: range of motion, maximum force, minimum force, and average force. Additionally or alternatively, the control system may be operable to display continuous readings of the angle data and force data measured on the output display.

Preferably, the goniometer may comprise an inclinometer that may be arranged to generate angle data representing the angular position of the body part with respect to gravity when it is in contact with the contact surface of the housing.

In one form, the force sensor may comprise a force transducer associated with the contact surface of the housing, the force transducer being arranged to generate force data representing the force applied to the contact surface by the body part. Preferably, the contact surface may be a contact pad that may be permanently fixed to the force transducer.

In another form, the force sensor may comprise a pressure transducer that is arranged to measure the pressure within a pressure component that comprises an enclosed substance and generate representative pressure data, the pressure component being located within the housing and being coupled to the contact surface of the housing such that any force applied to the contact surface by the body part causes the pressure within the pressure component to alter, the pressure data generated by the pressure transducer being converted into force data that represents a measure of the force applied to the contact surface by the body part. Preferably, the contact surface may be a contact pad that may be permanently fixed to the pressure component.

Preferably, the housing of the portable handheld device may comprise a rotatable hand piece for a user to grip.

In a second aspect, the present invention broadly consists in a portable system for measuring angles and forces associated with a joint of a person, comprising: a goniometer that is arranged to measure the angular position of a first side of the joint relative to a second side of the joint and generate representative angle data; a handheld force sensor that is arranged to measure the force applied by a body part associated with the joint and generate representative force data; and a control system that is arranged to operate the goniometer and handheld force sensor simultaneously, the control system also being arranged to receive simultaneous measurements of angle data and force data captured by the goniometer and handheld force sensor respectively.

Preferably, the control system may comprise external interfaces and may be operable to transfer the angle data and force data to external devices via the external interfaces Preferably, the control system may comprise memory and may be arranged to store the angle data and force data in the memory.

Preferably, the control system may comprise a user interface that may be operable by a user to control the goniometer and handheld force sensor and to manipulate the angle data and force data.

Preferably, the control system may comprise an output display that may be arranged to display the angle data and force data. For example, the control system may be operable to display the angle data and force data graphically against each other on the output display to provide an indication of the strength of the joint over a range of motion. Additionally or alternatively, the control system may be operable to display the angle data and force data graphically against time on the output display. Additionally or alternatively, the control system may be operable to process the angle data and force data to generate and display one or more discrete measurements on the output display, the discrete measurements comprising any one or more of the following: range of motion, maximum force, minimum force, and average force. Additionally or alternatively, the control system may be operable to display continuous readings of the angle data and force data measured on the output display.

Preferably, the control system may comprise an output device that ray be arranged to print the angle data and force data in various forms.

Preferably, the control system may comprise a personal computer.

In one form, the goniometer may comprise two members that are pivotally connected by a pivot connection having an associated angle sensor that is arranged to measure the angle between the members at the pivot connection, the two members being securable to body parts on opposite sides of the joint such that the angle sensor generates angle data representative of the relative angular position between the body parts on opposite sides of the joint.

In another form, the goniometer may comprise two units having notion sensors that are arranged to measure the path of the units in space, the two units being securable to body parts on opposite sides of the joint, the units being arranged to communicate with each other to generate angle data representative of the relative angular position between the body parts on opposite sides of the joint.

Preferably, the motion sensors of each unit may comprise accelerometers and magnetometers.

In one form, the handheld force sensor may comprise a hand piece, a contact surface that is arranged to contact a body part associated with the joint, and a force transducer coupled between the hand piece and contact surface, the force transducer being arranged to generate force data representing the force applied to the contact surface by the body part. Preferably, the force transducer may be a strain gauge, the hand piece being fixed to one end of the strain gauge and the contact surface being provided at the other end of the strain gauge. More preferably, the contact surface may be a contact pad that may be permanently fixed to an end of the force transducer.

In a third aspect, the present invention broadly consists in a portable handheld device for use by a therapist to measure angles and forces associated with a joint of a patient, comprising: a housing with a contact pad that is arranged to contact a body part associated with the joint and a hand piece for the therapist to grip; a goniometer mounted within housing that is arranged to measure the angular position of the body part when it is in contact with the contact pad of the housing and generate representative angle data; a force sensor mounted within the housing such that it is coupled to the contact pad, the force sensor being arranged to measure the force applied by the body part to the contact pad of the housing and generate representative force data; and a control system associated with the housing that is arranged to operate the goniometer and force sensor simultaneously to capture measurements of angle data and force data simultaneously.

Preferably, the control system may comprise external interfaces and may be operable to transfer the angle data and force data to external devices via the external interfaces.

Preferably, the control system may comprise memory and may be arranged to store the angle data and force data in the memory.

Preferably, the control system may comprise a user interface and an output display incorporated into the housing for displaying the angle data and force data, the user interface being operable by a user to control the device and the manner in which the angle data and force data is displayed on the output display.

Preferably, the goniometer may comprise an inclinometer that may be arranged to generate angle data representing the angular position of the body part with respect to gravity when it is in contact with the contact pad of the housing.

Preferably, the force sensor may comprise a force transducer that may be permanently fixed to the contact pad of the housing, the force transducer being arranged to generate force data representing the force applied to the contact pad by the body part associated with the joint.

Preferably, the hand piece may be rotatable relative to the housing.

In this specification and the accompanying claims, the term "therapist" is meant to include physiotherapists, physical therapists, or occupational therapists that are trained in maintaining and improving the movement and function of body parts, such as joints and limbs, but also extends to any other medical or sports practitioners.

In this specification and the accompanying claims, the term "patient" is intended to cover any person upon which the instrument of the invention is used.

In this specification and the accompanying claims, the phrase "portable system" is intended to cover any system that is self-contained and is able to be carried by a person, for example in a carry case or bag, or a mobile system that is capable of being moved from one place to another and that may be plugged in and/or semi-permanent.

In this specification and the accompanying claims, the term "goniometer" is intended to cover any instrument, device, component, sensor or the like that can measure angles, whether angular position or movement, associated with a body part or joint of a person.

In this specification and the accompanying claims, the phrases "angle data" and "force data" are intended to cover electronic data, whether analogue or digital, or any other forms of representing data.

The term 'comprising' as used in this specification and claims means 'consisting at least in part of', that is to say when interpreting statements in this specification and claims which include that term, the features, prefaced by that term in each statement, all need to be present but other features can also be present.

The invention consists in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF PREFERRED EMBODIMENTS

The present invention relates to a portable or mobile instrument for measuring parameters relating to the angular movement, angular position and strength of a body part or joint of a patient. In particular, the instrument may be utilised by a therapist to assess the patient's body part or joint by simultaneously capturing both joint angle and force data in a single test. The angle and force data can then be used to provide a measure of strength over the patient's range of motion or measures of range of motion and strength, such as maximum, minimum and average force. Further, the angle and force data can be correlated to provide measures of strength at particular angular positions.

Two preferred embodiments of the instrument will be described by way of example. FIGS. 1-11 relate to a first embodiment of the instrument in the form of a portable system, while FIGS. 12-17 relate to a second embodiment of the instrument in the form of a portable handheld device.

First Preferred Embodiment

Portable System

Figure 1:
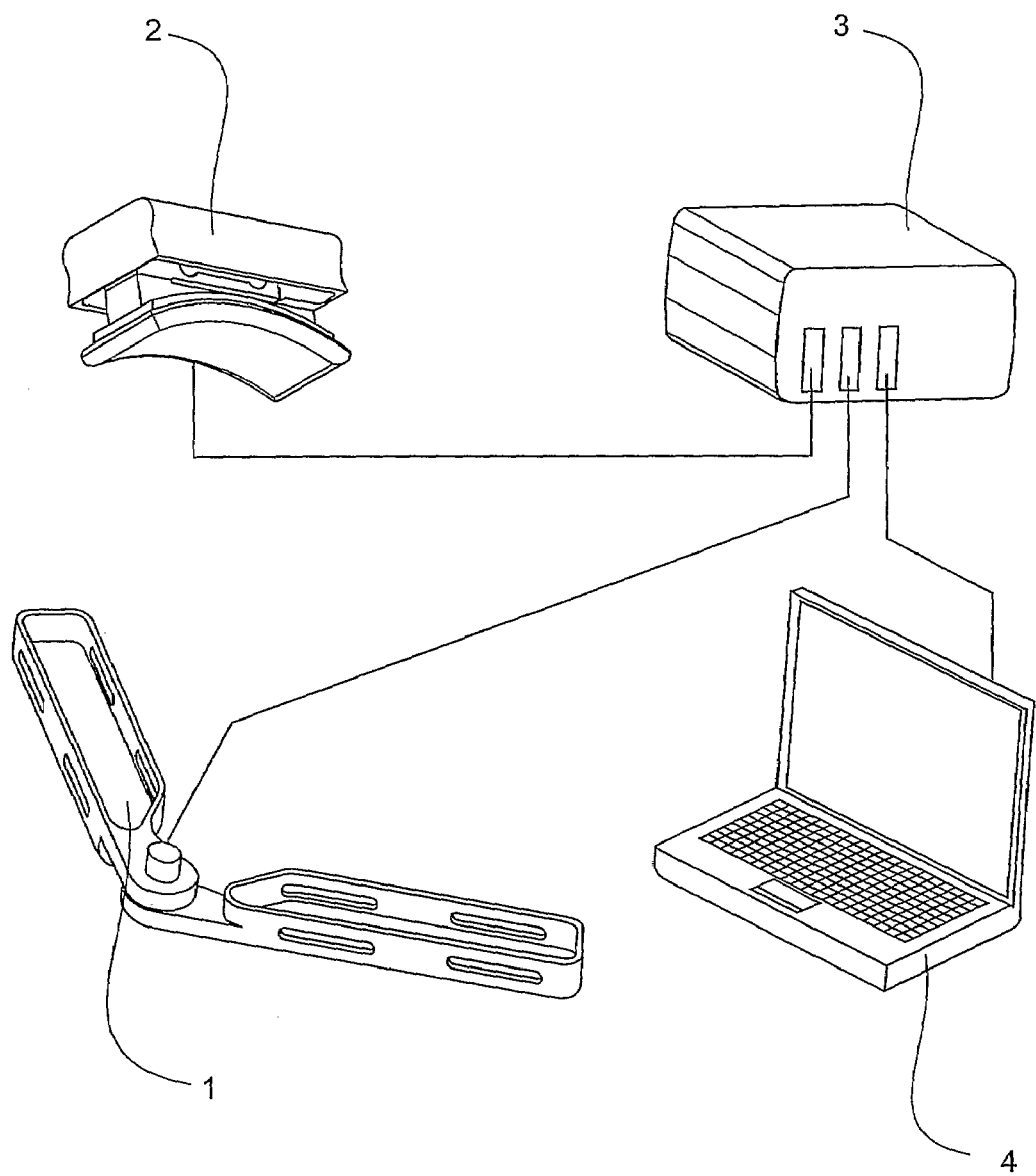
FIG. 1 shows a first embodiment of the present invention in the form of a portable system having a number of components.
Figure 2:
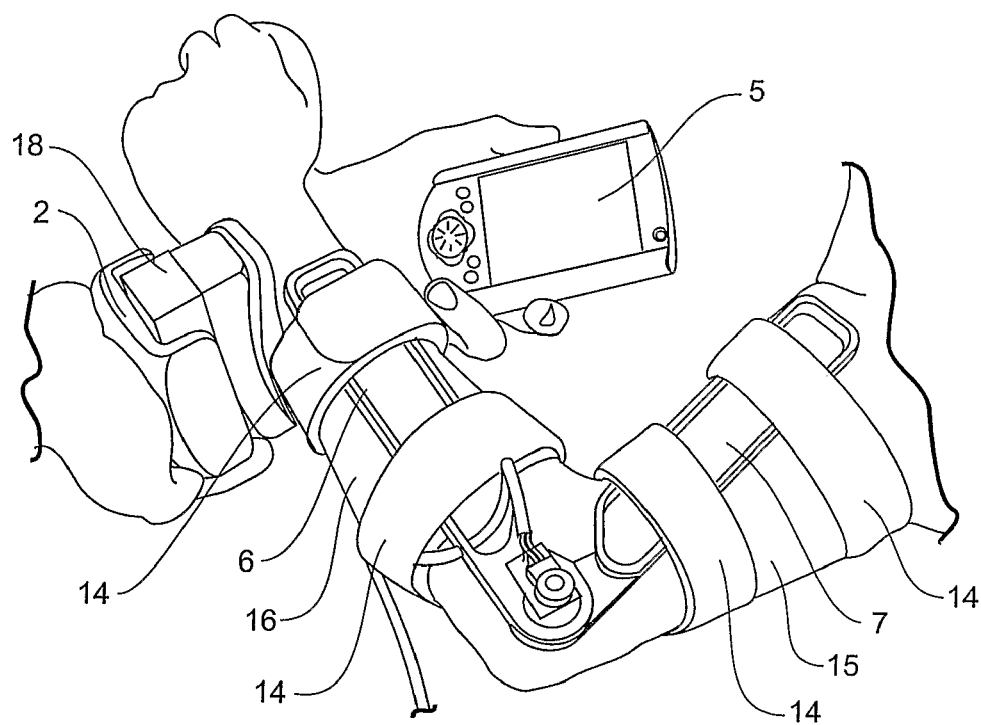
FIG. 2 shows the portable system being used to test an elbow joint of a patient.
Figure 3:
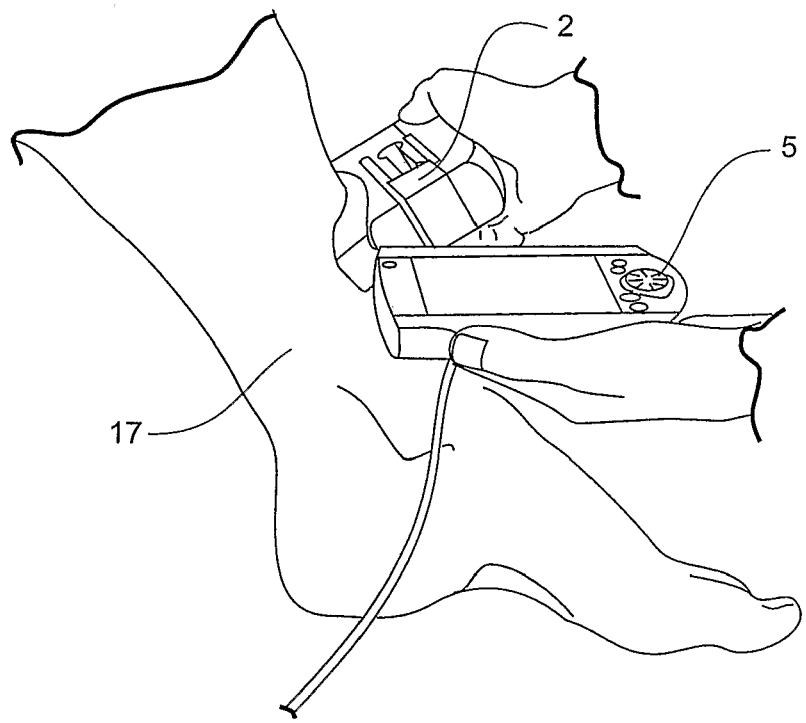
FIG. 3 shows a force sensor of the portable system in use on a lower leg of a patient.

Referring to FIGS. 1-3, the portable system form of the instrument includes a goniometer 1, a force sensor 2, a control box 3 and a user interface. The user interface may be a laptop computer 4 or alternatively a hand held computer 5 may be used.

Goniometer

Figure 6:
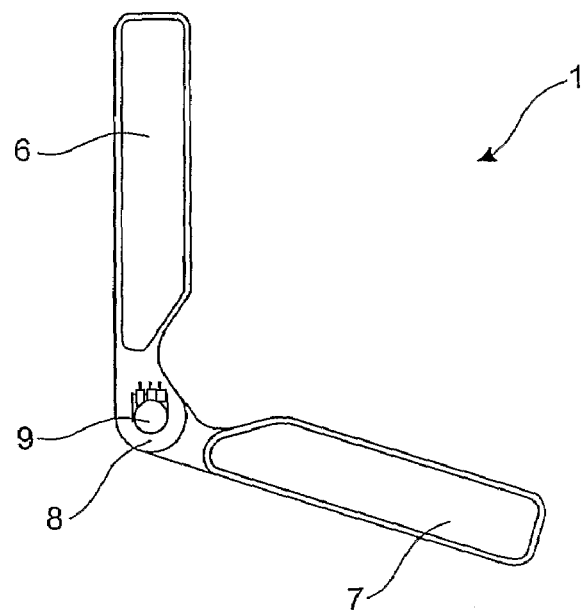
FIG. 6 shows a top view of a first form of goniometer utilised in the portable system.

A preferred form of the goniometer 1 of the instrument is shown in FIG. 6. The goniometer 1 is a simple device designed to measure the angle of a joint. It consists of two members 6, 7 connected by a pivot connection 8. An angle sensor in the form of a potentiometer 9 returns a voltage proportional to the angle of the pivotal connection. When used to measure elbow range of notion, for example, the goniometer 1 is secured to the arm of the subject with straps 14 as shown in FIG. 2. Each strap 14 is provided with releasable attachment means such as Velcro. The first member 6 is secured to the forearm 16 and the second member 7 is secured to the upper arm 15. The pivot connection 8 of the goniometer is aligned with the centre of rotation of the elbow joint. Alternatively, each member 6, 7 of the goniometer may be held in line with the patient's limbs by the therapist performing the test so that straps are not required.

The goniometer may also be secured to other parts of the subject's body, for example, a thigh and lower leg of a patient for measuring knee range of motion.

Preferably, the goniometer will take continuous readings, which may be displayed on an LCD display. The goniometer may have a hold button for locking the display. The goniometer may also have a tare button for zeroing the device at any chosen position of the patient's joint, for example in a half flexed position.

Figure 7:
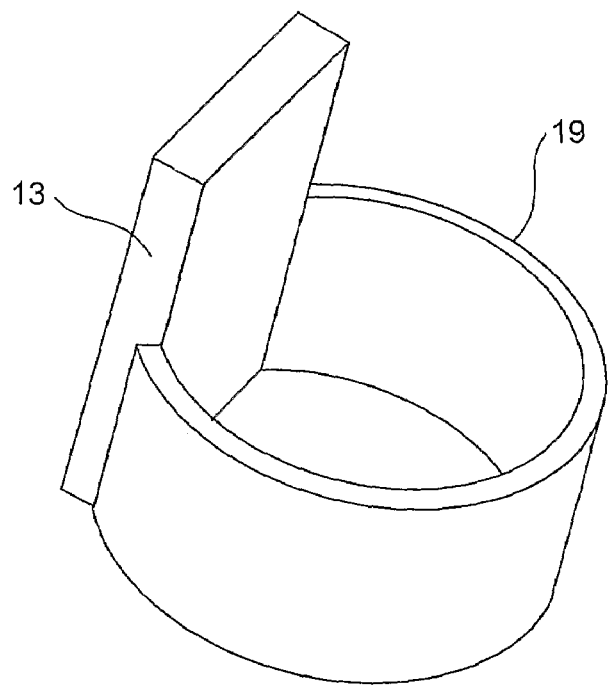
FIG. 7 shows a perspective view of a second form of goniometer utilised in the portable system.

In another preferred form, the goniometer may consist of two units that are not rigidly connected to each other. An example of one of these units 13 is shown in FIG. 7. In order to measure the range of motion of different joints of the body, such as the knee, elbow, shoulder or hip, each unit 13 may be attached to the limbs associated with that joint, i.e. the limbs on either side of the joint. The units 13 may be attached using straps 19 with releasable attachment means such as Velcro. Alternatively, each unit 13 may be held in line with the patient's limbs by the therapist who is performing the test. This allows the goniometer to be operated quickly, especially in situations where the therapist has limited time available with the patient.

Each unit 13 may be provided with a motion sensor comprising a selection of accelerometers and magnetometers. The gravitational field would provide one reference vector and the earth's magnetic field would provide another reference vector. The path of each unit 13 in space can be determined by using these references along with the integral of the acceleration vector. If two such units 13 are attached to the body part on opposite sides of the joint being measured, the difference in motion between the two units can be calculated and the virtual centre of rotation can be determined. This should correspond exactly with the axis of the joint being measured. It is then possible to calculate the angle of rotation of the joint relative to a zero configuration, for example, the arm held completely straight. Preferably, the two units 13 would communicate via a wireless radio link. However, any other wired or wireless communication method may be used.

Force Sensor—Handset

A preferred form of the force sensor 2 of the instrument is shown in FIG. 3. The force sensor 2 is in the form of a strength meter handset and is shown in use on the lower leg 17 of a patient.

Figure 4:
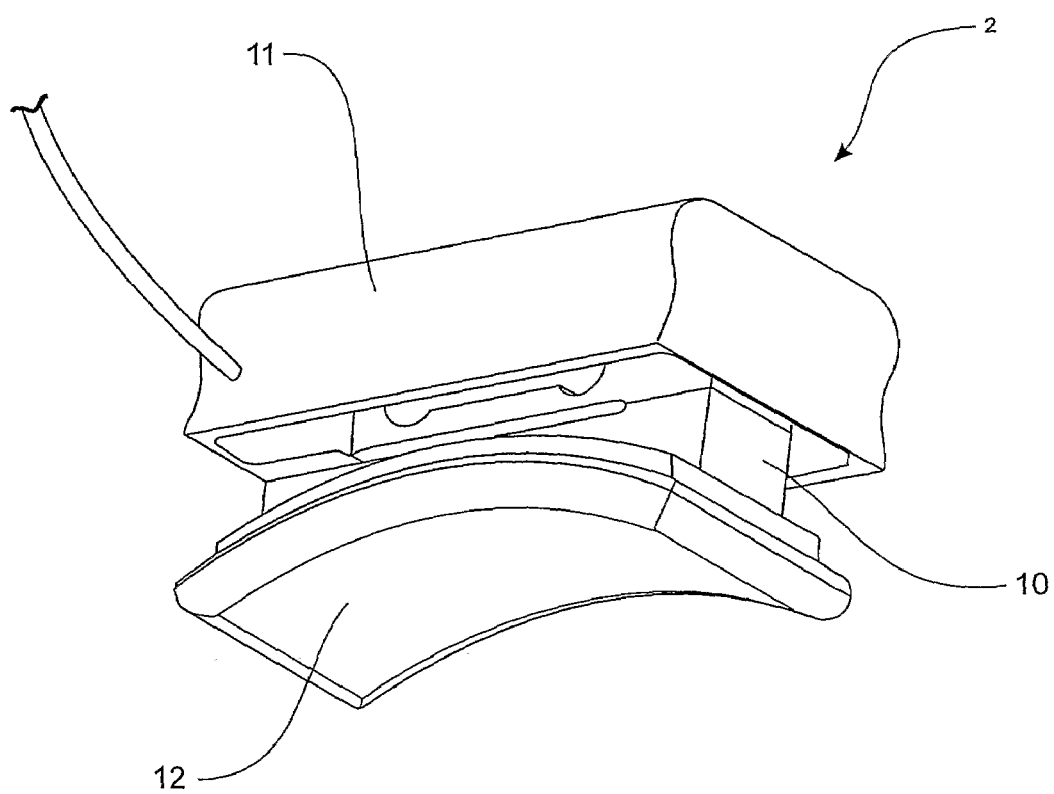
FIG. 4 shows a perspective view of the force sensor of the portable system.

Referring to FIG. 4, the preferred form handset includes a hand piece 11, a contact pad 12, and a force transducer, such as a strain gauge 10. The preferred form strain gauge 10 is capable of measuring up to 30 kg, but it will be appreciated that other strain gauges with higher or lower limits may be utilised in alternative forms of the handset. The strain gauge configuration is such that forces applied in axes other than the principal axis of the gauge are cancelled out in the output. This allows the therapist to align the gauge with the axis of interest and ignore other forces that the patient may produce.

One end of the strain gauge 10 is connected to the hand piece 11 shaped generally as shown in FIG. 4. The hand piece 11 is designed to transmit force from the therapist to the patient. It is broad and rounded for comfort, with a ridge around the edge for easy grasping. The hand piece 11 may be made from any material such as plastic, silicone rubber or an aluminium alloy. Depending on the use of the handset, the hand piece may be removed and replaced by another handle or hand piece when desired.

The opposite end of the strain gauge 10 is connected to a contact pad 12. The contact pad 12 has a shaped, padded compression surface that bears against the body part of the patient. Care has been taken to ensure that the padded surface prevents skin damage, even when the handset is tilted away from normal to the bearing surface on the patient. This is important because some patients will have decreased sensation in their limbs, and the consequences for pressure damage to skin are serious for such people. The contact pad 12 may be removed and replaced by another pad with a different shape depending on the use of the handset. For example, a contact pad for use on a forearm may have a curved shape corresponding to the shape of the forearm. This ensures maximum contact between the contact pad and the limb being tested. In contrast, a contact pad for use on other body parts may have a shallower or deeper curve or may be flat. It will be appreciated that the strain gauge may form a contact surface for the patient's body part and that a contact pad is not a requirement in alternative forms of the handset.

An extension of the concept of simple force measurement is to use the handset to measure torque produced by the limb. Some therapists may prefer to use torque as a signal and others may prefer to use force as the signal. Torque measurement can be achieved by a length measurement instrument such as a linear encoder that is attached from the force measurement handset to the limb pivot region. The length measurement instrument will measure the distance from the limb pivot point to the location of the force measuring handset on the patient's limb. The force measurement reading is electronically multiplied by the length measurement to produce a value of the torque that the patient's limb can achieve.

Preferably, the handset will take continuous readings that may be displayed on an LCD display 18 as shown in FIG. 2. The handset may have a hold button for locking the display. The handset may also have a tare button for zeroing the device at any chosen position of the patient's joint, for example in a half flexed position. The handset may further have a peak hold button for recording maximum force or other buttons for recording average or minimum forces.

Rather than having a large machine with an arm driven by a motor, as is the case on the isokinetic dynamometers, the handset is handheld and a force is applied by a therapist, as shown in FIGS. 2 and 3. The handset and goniometer are small in size and can be placed in a bag or carry case for transportation as a portable system. This allows tests to be performed in a number of different locations within a hospital or clinic for example.

If a hand held computer is used, it may also be placed in the bag or carry case for transportation. This allows the system to be self contained and readily moveable from place to place.

Alternatively, if a PC or laptop computer is used as the interface, the system is capable of being moved from one place to another and may be plugged into the PC or laptop computer.

Control Box

The control box 3 is arranged to supply power to the goniometer and force sensor. It also is arranged to receive angle data and force data simultaneously from the goniometer and force sensor respectively, along with communicating this data to the user interface.

The preferred embodiment of the control box 3 houses electronics to perform the following functions:

1. Power supply;
2. Strain gauge excitation;
3. Strain gauge amplification;
4. Strain gauge A/D;
5. Goniometer excitation;
6. Goniometer A/D; and
7. Digital output.

Figure 8:
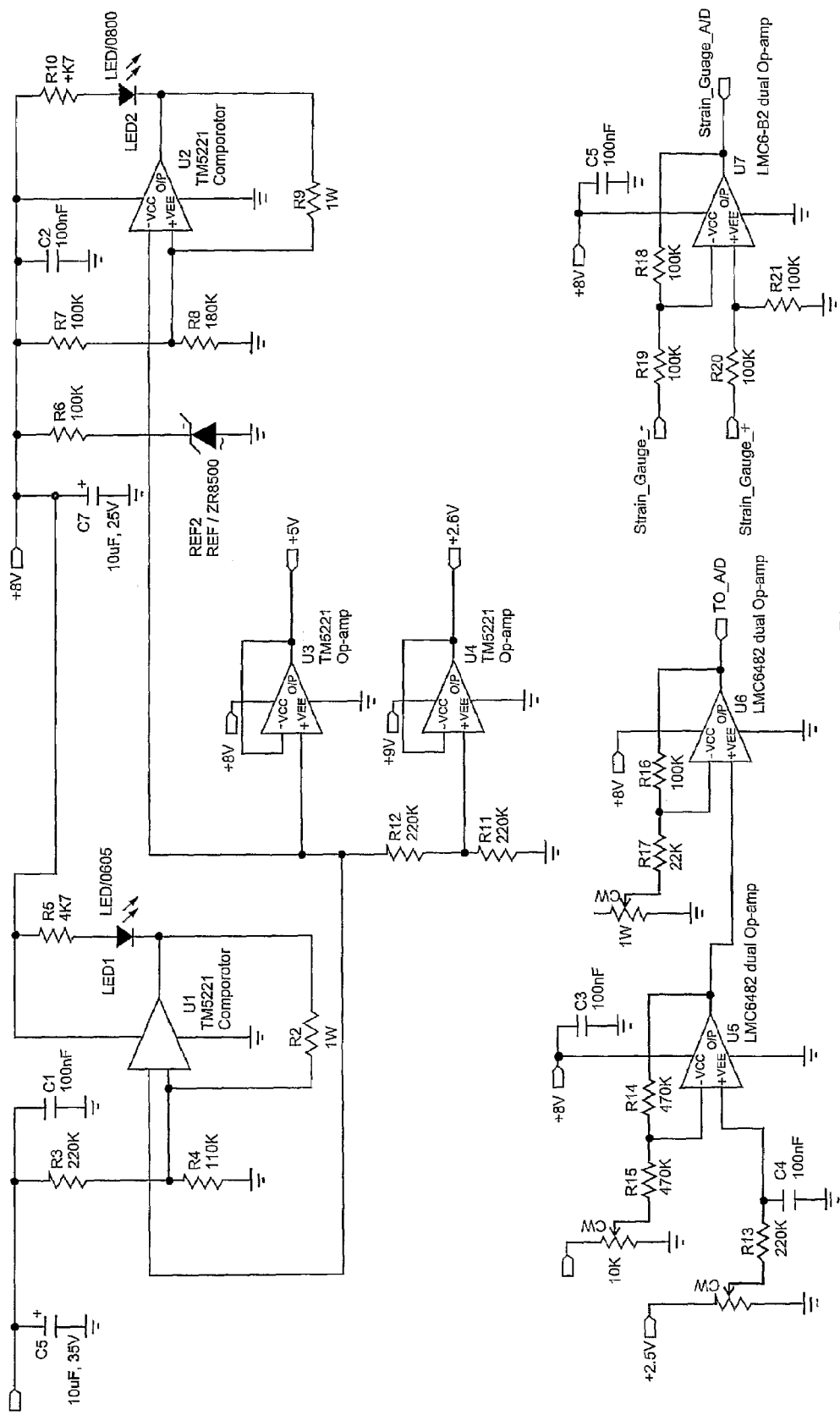
FIG. 8 shows an example electronic circuit that supplies excitation to the force sensor and goniometer.

FIG. 8 shows an example of an electronic circuit that was developed to supply excitation to the strain gauge 10 of the handset 2 and goniometer 1, and power the A/D board. Preferably, batteries provide the power supply that excites the strain gauge amplifier and the goniometer potentiometer pot.

Preferably, the goniometer signal is amplified by an adjustable factor and offset by an adjustable DC voltage. This allows the goniometer to be tuned to particular angular ranges and take advantage of the resolution of the A/D board. The strain gauge signal is buffered and sent to the A/D board.

User Interface

The user interface may be a laptop computer 4, handheld computer 5, or any other type or personal computer.

Figure 5:
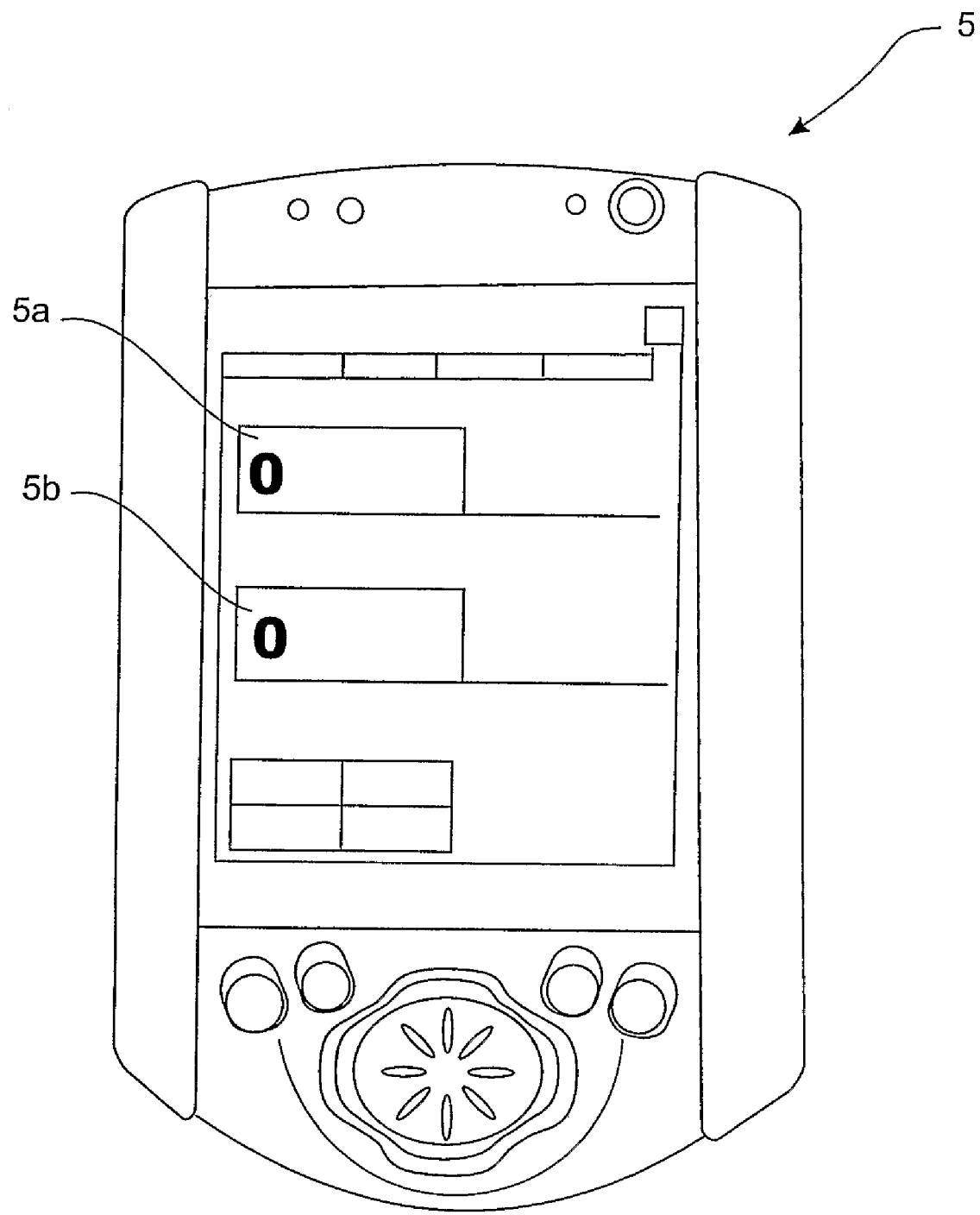
FIG. 5 shows a front view of a user interface of the portable system.

The first interface to be developed was a Compaq Pocket PC handheld computer 5 as shown in FIG. 5. The handheld computer is, by way of example, arranged to display readings of force 5a and angle 5b.

A second user interface was developed on a laptop computer 4. The larger screen and the extra speed of the laptop computer made it possible to provide multiple real time data displays. The computer could be placed on a desk and viewed during the test.

It will be appreciated that the user interface and control box may be integrated together as a control system if desired and that the control box or user interface may be arranged to store the angle and force data generated by the goniometer and force sensor. Further, there are various integrated or independent output devices that may be associated with the user interface or control box for printing and/or displaying the data.

Operation

When used to measure tricep strength, for example, the goniometer 1 is secured to the arm of the subject with straps 14. Each strap 14 is provided with releasable attachment means such as Velcro. The first member 6 is secured to the forearm and the second member 7 is secured to the upper arm. The pivot joint 8 of the goniometer 1 is aligned with the centre of rotation of the elbow joint.

The handset 2 is placed with the shaped, padded compression surface 12 against the surface of the forearm. The handset is operated by the therapist using the hand piece 11. The test begins with the elbow joint in a first position, for example, fully flexed. The therapist applies a force to the forearm using the handset and instructs the patient to resist the force being applied. The angle associated with the elbow joint and force applied by the therapist are recorded simultaneously and displayed on the user interface.

The instrument may be used to measure isokinetic forces. This involves the patient applying maximum force while the therapist moves the body part at a constant angular velocity about its joint. As the range of motion is carried out, the outputs are displayed on the user interface.

Alternatively, the instrument may be used to measure isometric forces. This involves the therapist applying the force at discrete angles and recording the force applied without substantial angular movement at the joint of the body part. Similarly, results are displayed on the user interface.

The angle and force data recorded during the tests may be plotted against each other to provide a measure of strength over a range of motion or both may be plotted against time. Alternatively, or additionally, the data may be used to provide discrete measures of range of motion and strength, such as maximum, minimum and average force. Further, the system may provide simultaneous and continuous readings of both angle and force data during the tests.

Example Tests

Portable System

Informal tests were carried out with the system on a patient having C5/6 incomplete tetraplegia, with reasonable bicep control but very weak triceps. There was also a marked strength imbalance between right and left arms of that patient.

Figure 9:
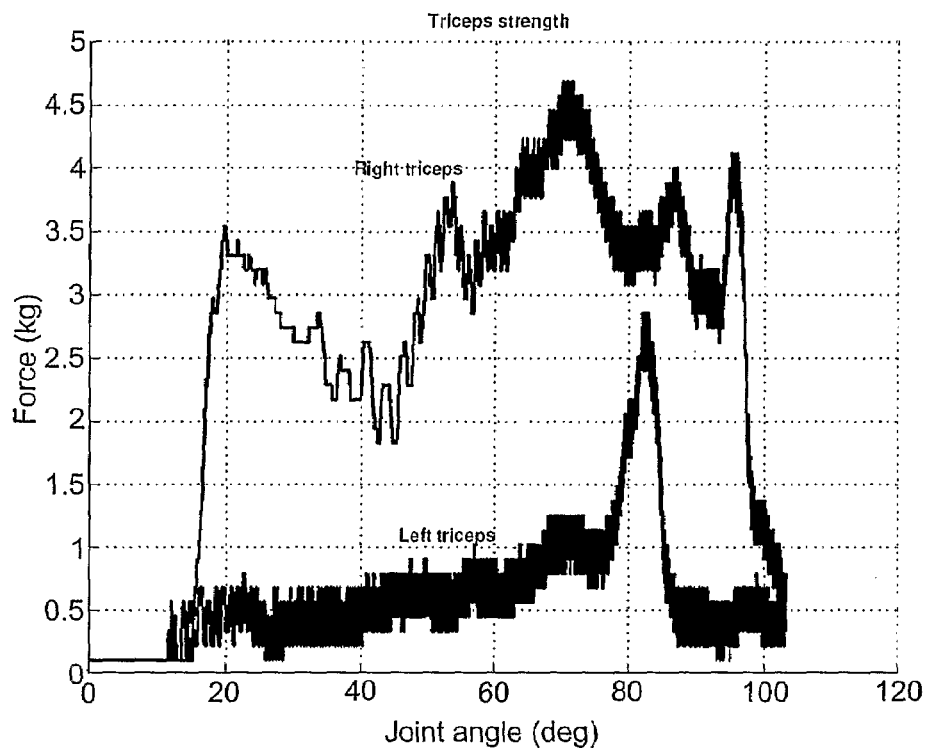
FIG. 9 shows readings taken from a patient with C5/6 incomplete tetraplegia.

Tests were performed on the arms, and the results are displayed in FIG. 9. The test results clearly display the patient's level of function. It can be seen that the patient has relatively weak triceps, with the left triceps being considerably weaker than the right and that the triceps strength occurs over a very small range of motion.

Note that for this test the arm begins fully flexed, and the joint angle decreases with time, thus the plots should be read right-to-left. Examining the trace for the left triceps, the patient displays the ability to exert a short burst of force at the beginning of the test, but cannot sustain it.

Figure 10:
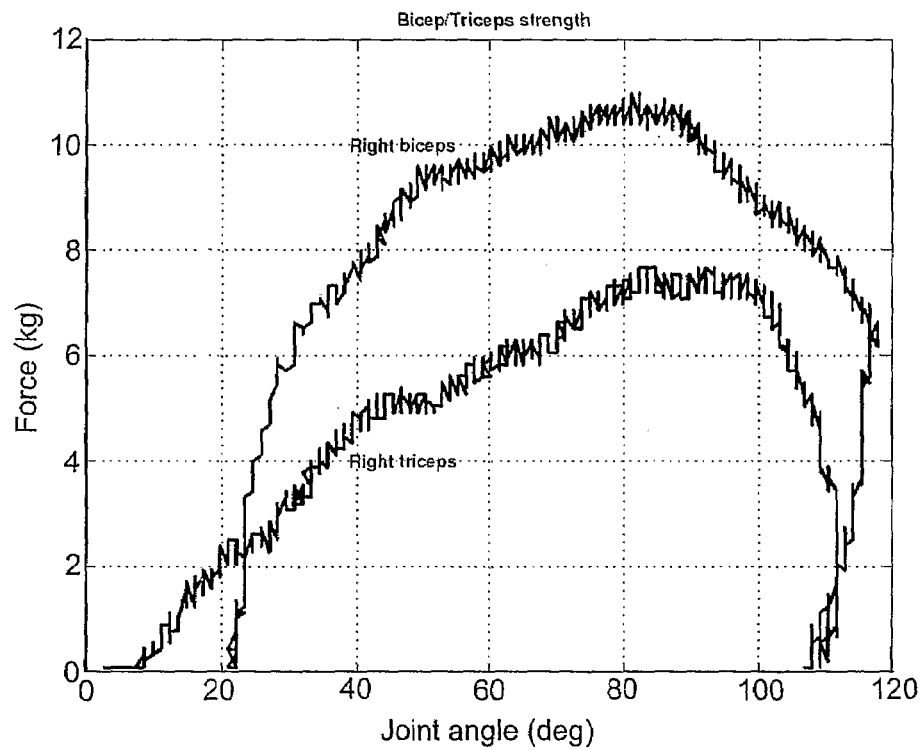
FIG. 10 shows readings taken from a patient with normal arm function.

FIG. 10 shows readings taken from a patient with normal arm function. As expected the strength of the arm is greatest around 90° because the mechanical advantage of the muscles is at its greatest there.

Figure 11:
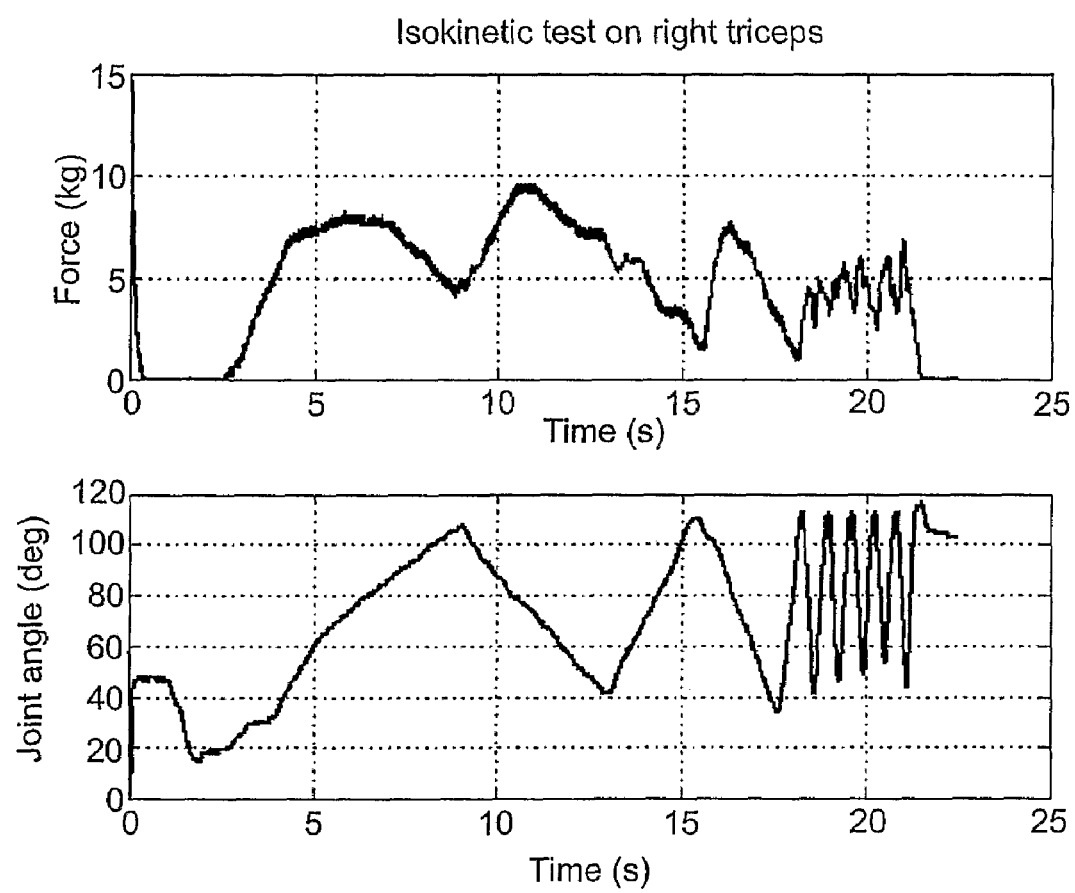
FIG. 11 shows the results of an isokinetic test carried out with the portable system on a patient with normal arm function.

FIG. 11 shows the results of an isokinetic test carried out with the instrument. The therapist must use a reasonable amount of skill to achieve the constant speed required, but it was found that it was possible to achieve a reasonable result with a little practise. The results are comparable to those obtained by an isokinetic dynamometer.

Second Preferred Embodiment

Portable Handheld Device

Referring to FIGS. 12-17, the portable handheld device form of the instrument includes a goniometer and a force sensor that are incorporated into a single housing and that are arranged to obtain continuous readings of both angle and force data simultaneously. A control system comprising, for example, control electronics, a rechargeable power supply, interfaces and an output display is also provided in the handheld device.

Figure 12:
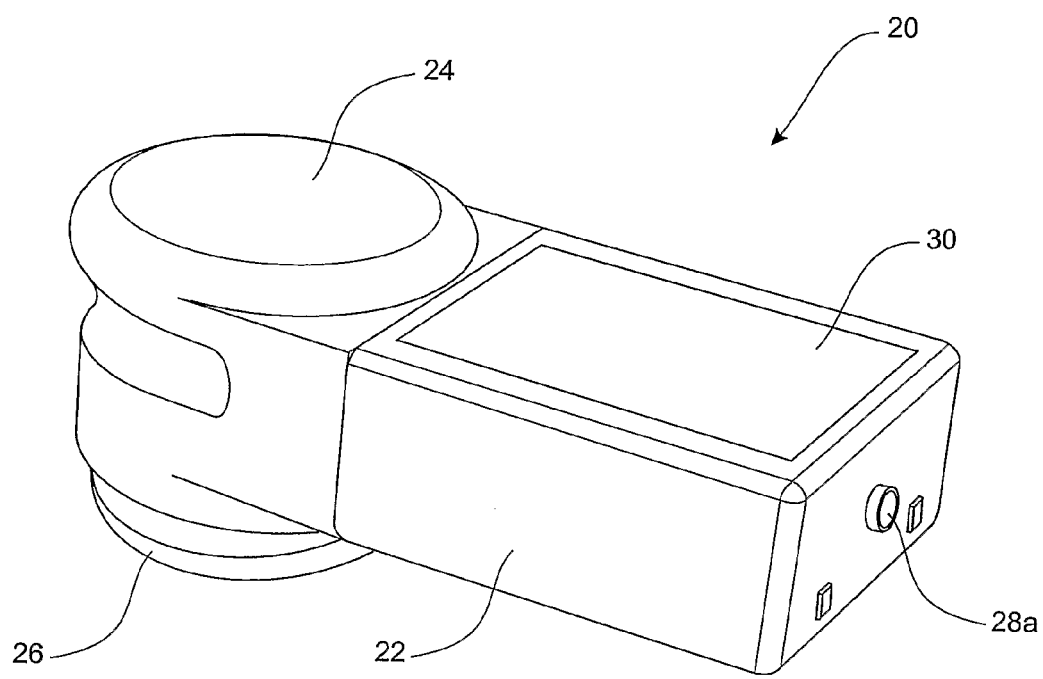
FIGS. 12-14 show perspective views of a second embodiment of the present invention in the form of a portable handheld device.
Figure 13:
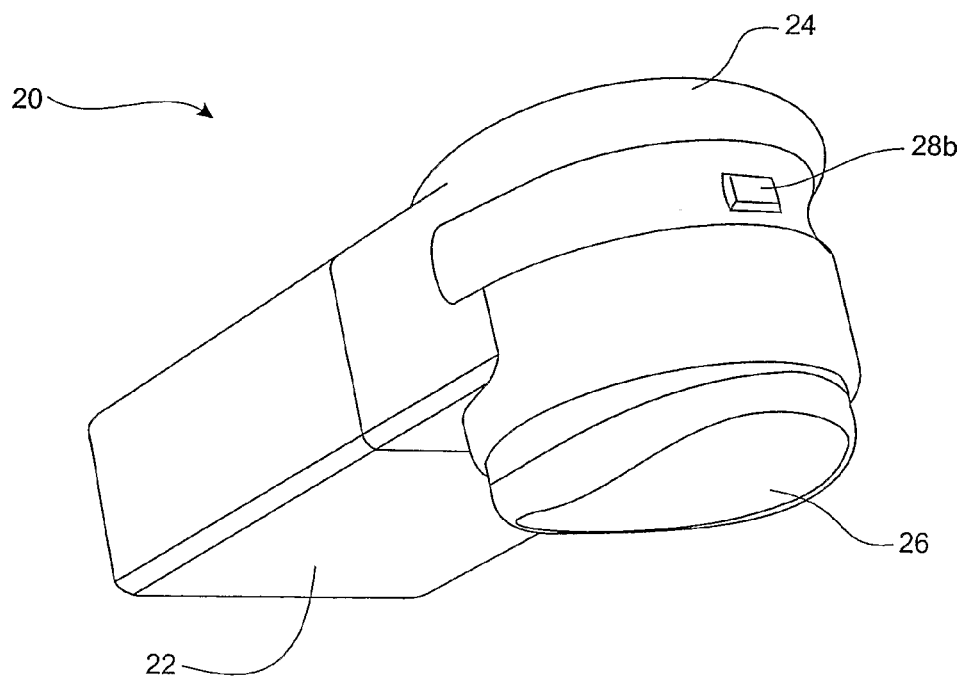
Figure 14:
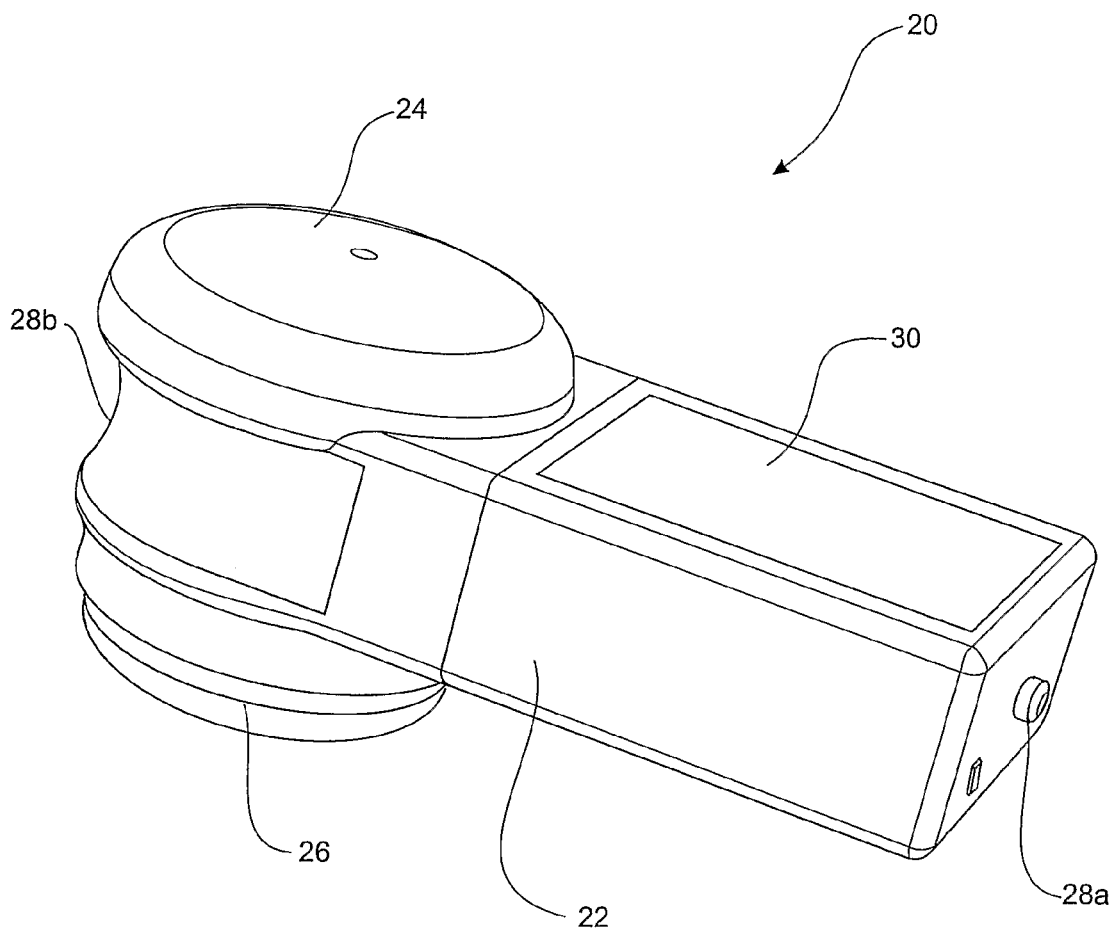

Referring to FIGS. 12-14, a preferred form of the handheld device 20 is shown. As mentioned, the housing 22 incorporates a goniometer and force sensor with associated control electronics for measuring angle and force data relating to the body part of a patient. The housing 22 includes a rotatable hand piece 24 for the therapist to grip and a contact pad 26 for bearing against a portion of the patient's body part that is being tested. A number of control buttons 28a, 28b and a display 30 are also provided.

In the preferred form, the goniometer is an inclinometer that communicates with the control electronics. The inclinometer is arranged to continuously monitor the angle of the handheld device 20 with respect to gravity when the contact pad 26 bears against the portion of the patient's body part that is being tested. The inclinometer generates angle data representing the angular movement or position of the body part being tested and this provides a measure of the range of motion of the body part and the associated joint. In particular, the inclinometer provides a measure of the angular movement of a joint of the body part, such as an elbow or knee joint for example. The measurement range and accuracy of the inclinometer will typically be in the order of 0 to 360°+/−1°. The inclinometer may, for example, be an electronic integrated circuit device that measures tilt with respect to gravity. In particular, the inclinometer may be based on an accelerometer, for example an STMicroelectronics EK3L02AQ three axis accelerometer, that measures the direction of gravitational pull of the earth and outputs that as three analogue signals that can be combined to produce an angle of tilt with respect to gravity. It will be appreciated that the goniometer component could alternatively be another type of inclinometer or electronic sensor, such as clinometer, tilt sensor or the like.

Figure 15:
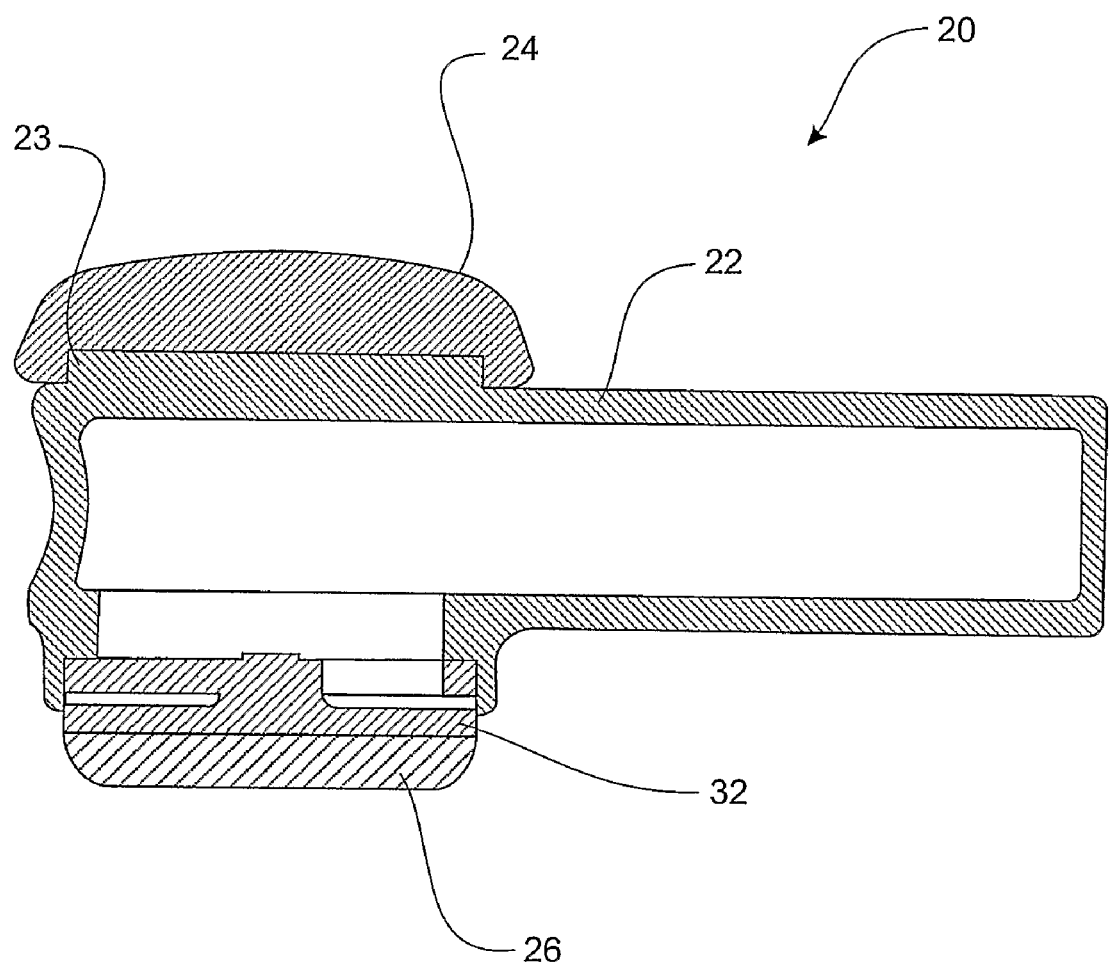
FIG. 15 shows a cross-sectional side view of the portable handheld device.
Figure 16:
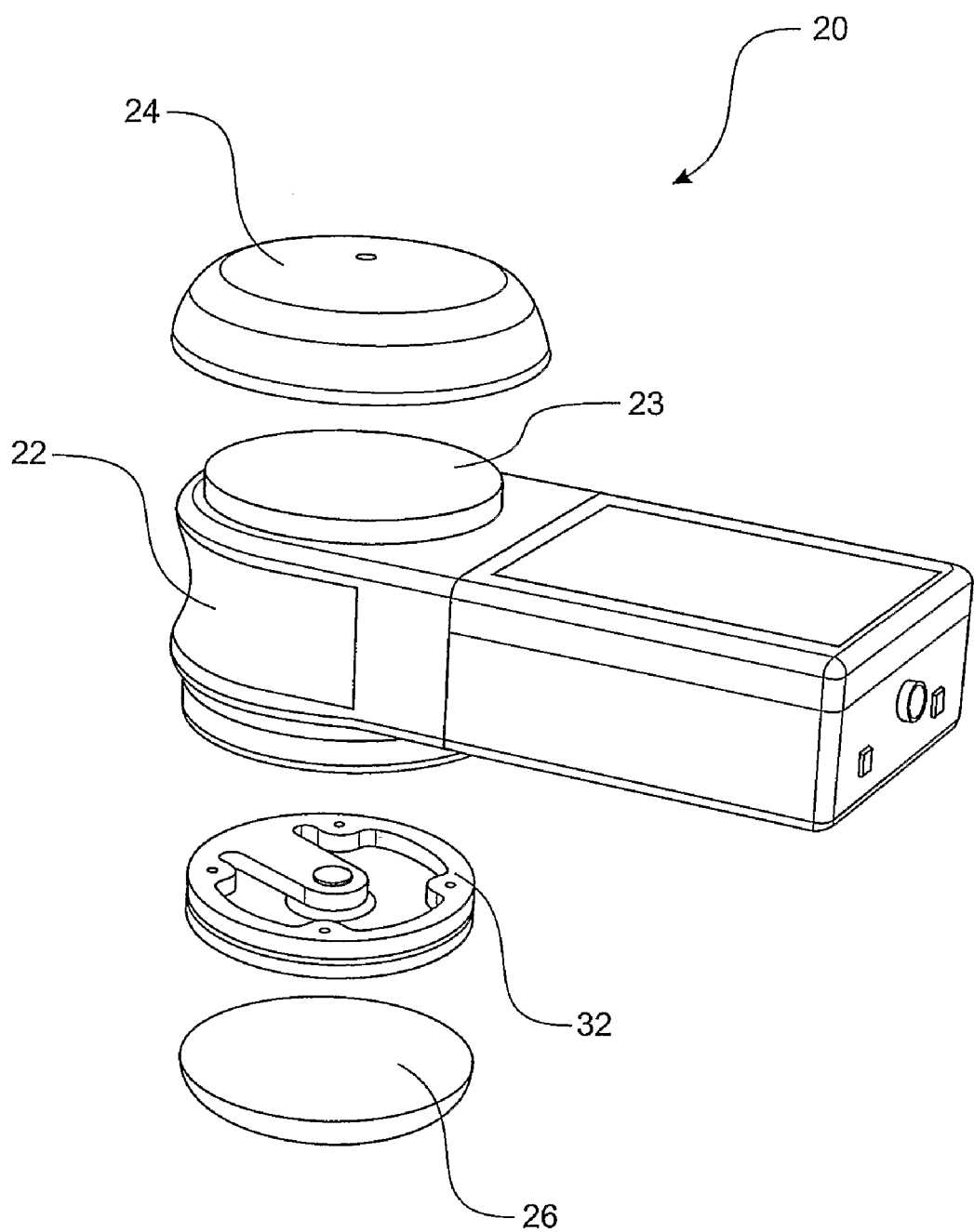
FIG. 16 shows a partially exploded perspective view of the portable handheld device.
Figure 17:
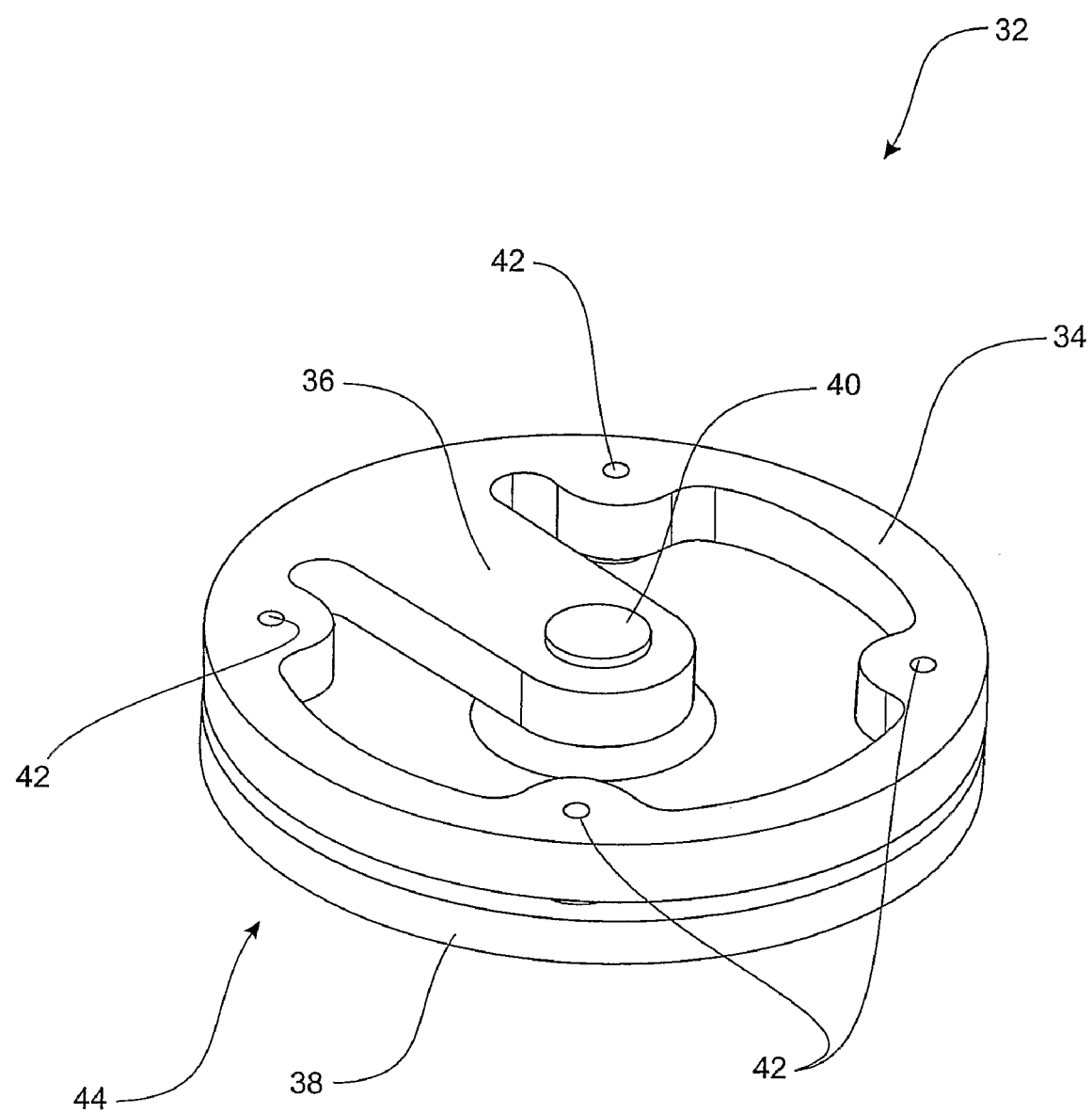
FIG. 17 shows a perspective view of a force transducer of the portable handheld device.

Referring to FIGS. 15-17, the preferred form force sensor comprises a contact pad 26 and a force transducer 32. The contact pad 26 may be attached to the force transducer 32 permanently or releasably. In the preferred form, the contact pad 26 is permanently connected to the force transducer 32 via adhesive or any other form of permanent mounting means. In alternative arrangements, the contact pad 26 may be releasably attached to the force transducer 32 by a coupling, which may be mechanical or any non-mechanical means such as a magnetic coupling or the like. For example, the contact pad 26 may be releasable to allow other shapes, sizes or forms of pads to be utilised for different patients and different body parts.

In operation, the contact pad 26 bears against a portion of the body part of the patient and the force transducer 32 is arranged to continuously measure the force applied to the contact pad 26 by the patient's body part to provide a measure of strength of an associated joint. From another perspective, the force transducer can be considered to measure the force applied to the patient's body part by the therapist as the patient resists the force. The force transducer 32 communicates the measured force data, having a typical measurement range and accuracy of 0 to 100 kg+/−100 g (or grams), to the control electronics for storage and/or processing.

In the preferred form, the contact pad 26 provides a shaped, padded compression surface for the patient's body part, but other types of force applicator could be utilised as alternatives. It will be appreciated that various shapes and sizes of the pad could be utilised and that the pads could be customised to conform to particular body parts, whether generally or for a specific patient. It will also be appreciated that the contact pad 26 is not essential to other alternative forms of the handheld device. For example, the force transducer may itself form a contact surface for the patient's body part.

Referring to FIG. 17, the preferred form force transducer 32 comprises a substantially annular ring 34 from which a beam 36 projects radially inward. The end of the beam 36 is coupled to a circular base plate 38 via an integral mounting pin 40. The contact pad 26 of the force sensor is attached to the lower surface 44 of the base plate 38. The mounting apertures 42 provided about the periphery of the annular ring 34 enable the force transducer 32 to be fixed within a recess of the housing 22 of the handheld device 20 via screws, nuts and bolts or the like. This arrangement ensures that the beam 36 supports the load when a patient pushes against the contact pad 26 and the therapist holds the handheld device 20 by its body. In operation, the beam 36 deforms slightly under the designed loadings and this deformation may be measured by strain gauges as described below. It will be appreciated that the force transducer may be secured within the housing utilising various other attachment means in alternative forms of the handheld device.

The force transducer 32 includes strain gauge resistors that are attached with adhesive onto both sides of the beam 36 at, for example, the point indicated by the pointer line 36. These strain gauges are arranged according to the electronic circuit shown in FIG. 8 to generate force data signals representing the force applied to the contact pad 26, thereby providing a measure of strength of a body part. The force transducer 32 is arranged to communicate the continuous force data to the control electronics for subsequent storage and/or processing.

An alternative form of force sensor for measuring strength may utilise a pressure transducer instead of a force transducer. In this form of force sensor, the contact pad 26 or force applicator may, for example, be fixed to a fluid filled bag component having a pressure transducer fitted within to measure and generate pressure data. The force exerted on the fluid filled bag, via the application of force to the contact pad 26, alters the pressure within the bag that is measured by the pressure transducer. The measured pressure data can then be calibrated and converted to generate force data representing the applied force. It will be appreciated that the fluid filled bag could alternatively be any other type of pressure component that comprises any type of substance, whether liquid or gas, the volume of which is enclosed by a membrane or other deformable material.

Referring to FIGS. 15 and 16, the preferred form hand piece 24 is rotatable and is connected to the housing 22 via a spigot joint coupler 23. In operation, the spigot joint coupler 23 allows movement of the therapist's hand relative to the patient's body part or limb during testing to enhance the accuracy of the measurements. For example, the rotatable hand piece 24 reduces the tendency for the measurements to be affected by any twist between the therapists hand and the patient's body part as the therapist presses the contact pad 26 of the handheld device 20 against the patient's body part via the rotatable hand piece 24.

As mentioned, the handheld device 20 has control electronics located within the housing 20. The control electronics control the goniometer and force sensor and receive the angle and force data measured. The control electronics may include a programmable microprocessor, memory, and an interface for the user and other external devices.

The user interface includes operable buttons 28a, 28b mounted on the housing 22 and a display 30 for presenting the measured data. The display 30 may also have touch screen capability to enable the therapist to operate the handheld device 20 via menu systems provided on the display 30. The display 30 may provide a touch screen menu as well as graphs or discrete values representing the obtained angle and force data. For example, the display 30 may be operable to generate a graph of force data versus angle data or force and angle data versus time. Further, discrete measures of range of motion or strength, such as maximum, minimum and average force or other continuous force and angle measurements may be generated and displayed. Additionally, the display may be operable to provide measures of strength at particular angular positions. Alternatively, the angle and force data may be transferred to another device for analysis, processing, display and printing.

The interface circuitry may also include input/output ports for communicating with external devices, such as computers, printers or other output devices, to transmit and receive data. Wireless modules may also be provided so that the handheld device may communicate with external devices over a wireless link.

The preferred form handheld device 20 has a rechargeable power supply, such as rechargeable batteries or a rechargeable battery pack. The power supply provides power to the goniometer, force sensor and the control electronics.

As mentioned, the control electronics receive the data measured by the goniometer and force sensor. The control electronics are then capable of processing the data for storage, transmission, display, or any combination thereof.

In the preferred form, the handheld device 20 can be used as a measuring device for muscle strength and range of motion, or alternatively it could be used to capture sets of data for subsequent storage and more detailed analysis on a PC. A PC can be used to display graphs of muscle strength with respect to range of motion or both strength and range of motion data against time. The connection to the PC may, for example, be a cradle that allows easy data exchange through say the computer's USB port or the like. The cradle may also act as a battery charger for the internal batteries in the handheld device 20.

Referring to FIGS. 12-14, the preferred form interface includes:

1. ON button 28a (auto switch off after 5 minutes of inactivity);
2. CAPTURE button 28b to begin storing data while holding in the correct start position;
3. A connection that plugs into the base charger module for communication with a PC; and
4. A DIGITAL DISPLAY 30 with a touch screen function that will provide the following:
   a) Display current angle and current force; and
   b) Touch screen buttons to zero the display, scroll and select from pre-programmed or downloaded menus.

The typical operation of the handheld device 20 will now be described. The handheld device 20 can be positioned and pressed against various body parts of the patient, such as limbs, to measure muscle force and angular position or movement of the limb, such as limb rotation with respect to gravity (i.e. in the vertical plane). For example, a therapist or other user presses the contact pad 26 of the handheld device 20 against the patient's limb via the rotatable hand piece 24 and then operates the handheld device 20, along with instructing the patient, to capture the desired force and angle measurements. By measuring and recording the force and angle of rotation as a combined signal, the therapist can determine how the strength of a joint changes through its range of motion. The therapist can also obtain measurements of the patient's range of motion and measures of maximum, minimum and average force over that range of motion or measures of strength at particular angular positions. The handheld device 20 can also be operated to obtain force and angle measurements independently if desired.

The operation of the instrument for readout or data acquisition can be programmed to meet specialist user requirements, but a general setup will now be explained by way of example only.

Data Presentation For Readout Application

1. When turned ON via ON button 28a, the digital screen 30 shows the current angle of rotation with respect to the previously stored reference plane. A vertical or horizontal reference position can be set if desired by placing the instrument on a vertical or horizontal surface and pressing the ZERO button provided on the display menu (touch screen);
2. When in use, the angle of rotation can be set to zero in any desired plane by pressing the ZERO button;

3. When turned ON, the digital screen 30 shows the current force being applied by the patient to the contact pad 26 (and being resisted by the therapist applying the instrument to the patient);
4. Pressing the CAPTURE button 28b at the start of a movement will automatically store the applied force and angular rotation to a default file;
5. The peak force applied during the movement can be viewed on the digital screen 30 by pressing the MENU button and selecting PEAK FORCE from the display menu (touch screen); and
6. The total angle of rotation for the movement can be viewed on the digital screen 30 by pressing the MENU button and selecting TOTAL ANGLE from the display menu (touch screen).

Data Acquisition

1. In addition to the above functions, continuous force versus angle of rotation data may be captured in up to, for example, 30 pre-loaded data sets that can be downloaded to a PC for analysis (typical graphs are shown in FIGS. 9-11 for the portable system embodiment);
2. Selected data set requirements for individual patients can be set up in a PC and downloaded into the handheld device 20 in named files prior to the start of a testing session;
3. The individual files can be viewed using the MENU button and selecting the file required from the display menu (touch screen);
4. The data set for the selected file can be deleted if required by pressing the MENU button and selecting CLEAR FILE and selecting the file that is to be deleted; and
5. The data sets for all the named files, or all the actual files, can be deleted by pressing the MENU button and selecting either CLEAR DATA or CLEAR FILES provided on the display menu (touch screen).

It will be appreciated that the handheld device 20 has a number of possible operations and can be used to perform a number of different tests, examples of which have been provided above. The handheld device 20 can be utilised to perform isokinetic and isometric tests on patients. For example, the handheld device 20 can be utilised to test the strength of a patient's limb over a range of motion. In particular, the handheld device 20 obtains angle and force data simultaneously during testing so that graphs such as those shown in FIGS. 9-11 can be generated for analysis. The angle and force data recorded may also be used to provide discrete measures of range of motion and strength, such as maximum, minimum and average force. It will be appreciated that the angle and force data may be processed, analysed and transferred to a computer for storage or future analysis in other ways also. The handheld device 20 can also be arranged to operate as either a strength measurement device or a range of motion measurement device in isolation.

In summary, the instrument of the invention, whether in the form of a portable system or a portable handheld device, is operable to obtain continuous measures of both strength and range of motion for a patient's body part simultaneously during a single test, of which there are many different types. The angle and force data measured by the instrument can then be used to provide strength over range of motion information, discrete measures of range of motion at a joint, discrete measures of strength, such as maximum, minimum and average force, or other continuous force and angle readings.

The instrument of the invention will most likely be utilised by physiotherapists when assessing the abilities and progress of their patients after injuries or during rehabilitation. However, it will be appreciated that the instrument may also be utilised in non-remedial applications such as sports assessments and the like.

Preferred embodiments of the invention have been described by way of example only. Modifications may be made thereto without departing from the scope of the invention as defined by the accompanying claims.

The invention claimed is:

1. A portable handheld device for measuring angles and forces associated with a joint of a person, comprising:
    a housing with a contact surface that is arranged to contact a body part associated with the joint;
    a goniometer associated with the housing that is arranged to measure the angular position of the body part when it is in contact with the contact surface of the housing and generate representative angle data;
    a force sensor associated with the housing that is arranged to measure the force applied by the body part to the contact surface of the housing and generate representative force data; and
    a control system associated with the housing that is arranged to operate the goniometer and force sensor simultaneously to capture measurements of angle data and force data simultaneously.

2. A portable handheld device according to claim 1 wherein the control system comprises external interfaces and is operable to transfer the angle data and force data to external devices via the external interfaces.

3. A portable handheld device according to claim 1 wherein the control system comprises memory and is arranged to store the angle data and force data in the memory.

4. A portable handheld device according to claim 1 wherein the control system comprises a user interface that is operable by a user to control the device and manipulate the angle data and force data.

5. A portable handheld device according to claim 1 wherein the control system comprises an output display that is incorporated into the housing to display the angle data and force data.

6. A portable handheld device according to claim 5 wherein the control system is operable to display the angle data and force data graphically against each other on the output display to provide an indication of the strength of the joint over a range of motion.

7. A portable handheld device according to claim 5 wherein the control system is operable to display the angle data and force data graphically against time on the output display.

8. A portable handheld device according to claim 5 wherein the control system is operable to process the angle data and force data to generate and display one or more discrete measurements on the output display, the discrete measurements comprising any one or more of the following: range of motion, maximum force, minimum force, and average force.

9. A portable handheld device according to claim 5 wherein the control system is operable to display continuous readings of the angle data and force data measured on the output display.

10. A portable handheld device according to claim 1 wherein the goniometer comprises an inclinometer that is arranged to generate angle data representing the angular position of the body part with respect to gravity when it is in contact with the contact surface of the housing.

11. A portable handheld device according to claim 1 wherein the force sensor comprises a force transducer associated with the contact surface of the housing, the force transducer being arranged to generate force data representing the force applied to the contact surface by the body part.

12. A portable handheld device according to claim 11 wherein the contact surface is a contact pad that is permanently fixed to the force transducer.

13. A portable handheld device according to claim 1 wherein the force sensor comprises a pressure transducer that is arranged to measure the pressure within a pressure component that comprises an enclosed substance and generate representative pressure data, the pressure component being located within the housing and being coupled to the contact surface of the housing such that any force applied to the contact surface by the body part causes the pressure within the pressure component to alter, the pressure data generated by the pressure transducer being converted into force data that represents a measure of the force applied to the contact surface by the body part.

14. A portable handheld device according to claim 13 wherein the contact surface is a contact pad that is permanently fixed to the pressure component.

15. A portable handheld device according to claim 1 wherein the housing comprises a rotatable hand piece for a user to grip.

16. A portable system for measuring angles and forces associated with a joint of a person, comprising:
a goniometer that is arranged to measure the angular position of a first side of the joint relative to a second side of the joint and generate representative angle data;
a handheld force sensor that is arranged to measure the force applied by a body part associated with the joint and generate representative force data; and
a control system that is arranged to operate the goniometer and handheld force sensor simultaneously, the control system also being arranged to receive simultaneous measurements of angle data and force data captured by the goniometer and handheld force sensor respectively.

17. A portable system according to claim 16 wherein the control system comprises external interfaces and is operable to transfer the angle data and force data to external devices via the external interfaces.

18. A portable system according to claim 16 wherein the control system comprises memory and is arranged to store the angle data and force data in the memory.

19. A portable system according to claim 16 wherein the control system comprises a user interface that is operable by a user to control the goniometer and handheld force sensor and to manipulate the angle data and force data.

20. A portable system according to claim 16 wherein the control system comprises an output display that is arranged to display the angle data and force data.

21. A portable system according to claim 20 wherein the control system is operable to display the angle data and force data graphically against each other on the output display to provide an indication of the strength of the joint over a range of motion.

22. A portable system according to claim 20 wherein the control system is operable to display the angle data and force data graphically against time on the output display.

23. A portable system according to claim 20 wherein the control system is operable to process the angle data and force data to generate and display one or more discrete measurements on the output display, the discrete measurements comprising any one or more of the following: range of motion, maximum force, minimum force, and average force.

24. A portable system according to claim 20 wherein the control system is operable to display continuous readings of the angle data and force data measured on the output display.

25. A portable system according to claim 16 wherein the control system comprises an output device that is arranged to print the angle data and force data in various forms.

26. A portable system according to claim 16 wherein the control system comprises a personal computer.

27. A portable system according to claim 16 wherein the goniometer comprises two members that are pivotally connected by a pivot connection having an associated angle sensor that is arranged to measure the angle between the members at the pivot connection, the two members being securable to body parts on opposite sides of the joint such that the angle sensor generates angle data representative of the relative angular position between the body parts on opposite sides of the joint.

28. A portable system according to claim 16 wherein the goniometer comprises two units having motion sensors that are arranged to measure the path of the units in space, the two units being securable to body parts on opposite sides of the joint, the units being arranged to communicate with each other to generate angle data representative of the relative angular position between the body parts on opposite sides of the joint.

29. A portable system according to claim 28 wherein the motion sensors of each unit comprise accelerometers and magnetometers.

30. A portable system according to claim 16 wherein the handheld force sensor comprises a hand piece, a contact surface that is arranged to contact a body part associated with the joint, and a force transducer coupled between the hand piece and contact surface, the force transducer being arranged to generate force data representing the force applied to the contact surface by the body part.

31. A portable system according to claim 30 wherein the force transducer is a strain gauge, the hand piece being fixed to one end of the strain gauge and the contact surface being provided at the other end of the strain gauge.

32. A portable system according to claim 30 wherein the contact surface is a contact pad that is permanently fixed to an end of the force transducer.

33. A portable handheld device for use by a therapist to measure angles and forces associated with a joint of a patient, comprising:
a housing with a contact pad that is arranged to contact a body part associated with the joint and a hand piece for the therapist to grip;
a goniometer mounted within housing that is arranged to measure the angular position of the body part when it is in contact with the contact pad of the housing and generate representative angle data;
a force sensor mounted within the housing such that it is coupled to the contact pad, the force sensor being arranged to measure the force applied by the body part to the contact pad of the housing and generate representative force data; and
a control system associated with the housing that is arranged to operate the goniometer and force sensor simultaneously to capture measurements of angle data and force data simultaneously.

34. A portable handheld device according to claim 33 wherein the control system comprises external interfaces and is operable to transfer the angle data and force data to external devices via the external interfaces.

35. A portable handheld device according to claim 33 wherein the control system comprises memory and is arranged to store the angle data and force data in the memory.

36. A portable handheld device according to claim 33 wherein the control system comprises a user interface and an output display incorporated into the housing for displaying the angle data and force data, the user interface being operable by a user to control the device and the manner in which the angle data and force data is displayed on the output display.

37. A portable handheld device according to claim 33 wherein the goniometer comprises an inclinometer that is arranged to generate angle data representing the angular position of the body part with respect to gravity when it is in contact with the contact pad of the housing.

38. A portable handheld device according to claim 33 wherein the force sensor comprises a force transducer that is permanently fixed to the contact pad of the housing, the force transducer being arranged to generate force data representing the force applied to the contact pad by the body part associated with the joint.

39. A portable handheld device according to claim 33 wherein the hand piece is rotatable relative to the housing.

* * * * *